US010646021B2

(12) United States Patent
Daifallah

(10) Patent No.: US 10,646,021 B2
(45) Date of Patent: May 12, 2020

(54) REFILLABLE ABSORBENT SWAB APPLICATOR PEN

(71) Applicant: Miriam F Daifallah, Oak Lawn, IL (US)

(72) Inventor: Miriam F Daifallah, Oak Lawn, IL (US)

(*) Notice: Subject to any disclaimer, the term of this patent is extended or adjusted under 35 U.S.C. 154(b) by 34 days.

(21) Appl. No.: 15/909,948

(22) Filed: Mar. 1, 2018

(65) Prior Publication Data

US 2018/0249810 A1 Sep. 6, 2018

Related U.S. Application Data

(60) Provisional application No. 62/465,467, filed on Mar. 1, 2017.

(51) Int. Cl.
*A45D 40/28* (2006.01)
*A61F 13/38* (2006.01)
*A45D 40/20* (2006.01)
*A45D 40/26* (2006.01)
*A45D 29/00* (2006.01)
*A45D 34/04* (2006.01)

(52) U.S. Cl.
CPC .......... *A45D 40/28* (2013.01); *A45D 40/20* (2013.01); *A45D 40/205* (2013.01); *A45D 40/262* (2013.01); *A61F 13/38* (2013.01); *A45D 29/007* (2013.01); *A45D 34/042* (2013.01); *A45D 2040/204* (2013.01); *A45D 2040/207* (2013.01); *A45D 2200/10* (2013.01); *A45D 2200/1009* (2013.01); *A45D 2200/1018* (2013.01)

(58) Field of Classification Search
CPC ...... A45D 29/007; A45D 29/17; A45D 40/26; A45D 40/28; A45D 40/205; A45D 40/207; A45D 40/208; A45D 40/262; A45D 34/04; A45D 34/042; A45D 2200/10; A45D 2200/1009; A45D 2200/1018; A45D 2200/1036; A45D 2200/1063; A61F 13/38
USPC ........ 15/104.94, 209.1, 210.1, 244.1; 604/1; 132/294, 313, 314, 317, 318, 320; 401/55, 57, 63, 65, 82, 85, 89, 90, 98
See application file for complete search history.

(56) References Cited

U.S. PATENT DOCUMENTS

| | | | | |
|---|---|---|---|---|
| 4,699,161 A * | 10/1987 | Smith | ................ | A45D 29/007 132/73.5 |
| 4,854,761 A * | 8/1989 | Smith | ................ | A45D 29/007 401/196 |
| 5,299,341 A * | 4/1994 | Wakao | ................ | A47L 25/00 15/184 |
| 6,551,265 B1 * | 4/2003 | Miguel | ................ | B43K 8/00 401/57 |
| 9,011,031 B2 * | 4/2015 | Jang | ................ | A45D 34/00 206/515 |
| 2010/0065576 A1 * | 3/2010 | Verheij | ................ | A45D 34/00 221/42 |
| 2015/0320503 A1 * | 11/2015 | Bezdikian | ................ | A61B 90/70 422/22 |

* cited by examiner

*Primary Examiner* — Mark Spisich

(57) ABSTRACT

A refillable absorbent swab applicator pen has a pen shell, a plurality of absorbent swab cartridges, and a cartridge advancement mechanism. The plurality of absorbent swab cartridges are positioned within the pen shell, and the cartridge advancement mechanism is integrated into the pen shell in order to advance the absorbent swab cartridges toward a dispensing end in order to expose a swab for use or discard a swab after use.

1 Claim, 4 Drawing Sheets

REFILLABLE ABSORBENT SWAB APPLICATOR PEN

The current application claims a priority to the U.S. Provisional Patent application Ser. No. 62/465,467 filed on Mar. 1, 2017.

FIELD OF THE INVENTION

The present invention relates generally to cosmetics. More particularly, the present invention relates to tools for cosmetic application tools.

BACKGROUND OF THE INVENTION

Cosmetics are substances or products used to enhance or alter the appearance or fragrance of the body. Many cosmetics are designed for use of applying to the face and hair. They are generally mixtures of chemical compounds; some being derived from natural sources (such as coconut oil), and some being synthetics. Common cosmetics include lipstick, mascara, eye shadow, foundation, rouge, skin cleansers and skin lotions, shampoo, hairstyling products (gel, hair spray, etc.), perfume and cologne. Cosmetics applied to the face to enhance its appearance are often called make-up or makeup. In the U.S., the Food and Drug Administration (FDA), which regulates cosmetics, defines cosmetics as "intended to be applied to the human body for cleansing, beautifying, promoting attractiveness, or altering the appearance without affecting the body's structure or functions".

Cosmetics are intended to be applied externally. They include, but are not limited to, products that can be applied to the face: skin-care creams, lipsticks, eye and facial makeup, towelettes, and colored contact lenses; to the body: deodorants, lotions, powders, perfumes, baby products, bath oils, bubble baths, bath salts, and body butters; to the hands/nails: fingernail and toe nail polish, and hand sanitizer; to the hair: permanent chemicals, hair colors, hair sprays, and gels.

A subset of cosmetics is called "makeup", refers primarily to products containing color pigments that are intended to alter the user's appearance. Manufacturers may distinguish between "decorative" and "care" cosmetics.

Cosmetics that are meant to be used on the face and eye area are usually applied with a brush, a makeup sponge, the user's fingertips, or using other tools such as cotton pads, swabs or other portions of absorbent material which initially absorb the cosmetic product to be applied, and subsequently transfers the cosmetic product to the user's face or other area of application upon physical contact.

Cotton swabs consist of a small wad of cotton wrapped around one or both ends of a short rod, usually made of either wood, rolled paper or plastic. They are commonly used in a variety of applications including first aid, cosmetics application, cleaning, and arts and crafts. Cotton swabs are often used in applying and removing makeup, in addition to other cosmetics uses such as touching up nail polish.

Makeup and other cosmetics users may encounter the need to apply, re-apply or otherwise adjust their current configuration of cosmetics application while running errands, visiting friends, or other on-the-go similar situations. Thus, a cosmetic applicator tool is desired that is portable and can be kept anywhere, such as in a purse, luggage, or makeup tote. It is therefore an objective of the present invention to present a cosmetics applicator pen that is capable of dispensing single use cotton swab cartridges and is refillable.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

Figure 1:
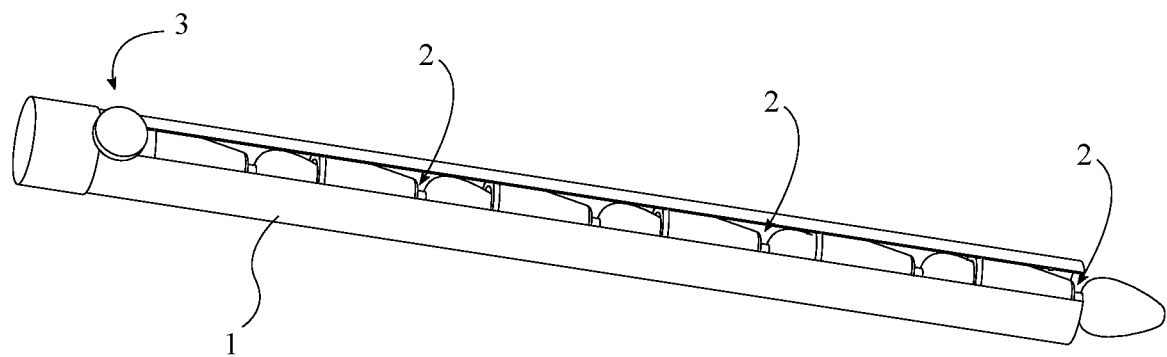
FIG. 1 is a perspective view of an embodiment of the present invention.
Figure 2:
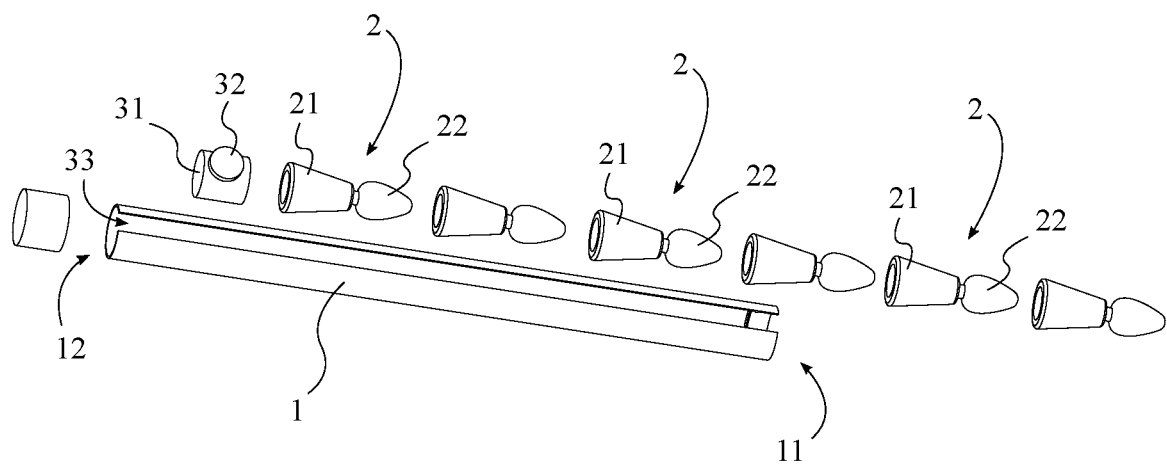
FIG. 2 is an exploded perspective view of an embodiment of the present invention.

The present invention is a refillable absorbent swab applicator pen that is able to dispense single use, disposable absorbent swab units for convenience in applying or correcting cosmetics. Referring to FIGS. 1-2, in general, the present invention comprises a pen shell 1, a plurality of absorbent swab cartridges 2, and a cartridge advancement mechanism 3.

The pen shell 1 is the main structural component of the present invention. Preferably, the pen shell 1 is an elongated, hollow body with a cylindrical cross section, though it is noted that other cross-sectional geometries may be comprised in other embodiments. The pen shell 1 comprises a dispensing end 11 and a refill end 12, with the pen shell 1 extending between the dispensing end 11 and the refill end 12. The pen shell 1 acts as a reservoir tube, preferably capable of containing 20 or more absorbent swab cartridges 2.

Each of the plurality of absorbent swab cartridges 2 is a small modular unit designed to be inserted into and dispensed from within the pen shell 1, and to fit between other cartridges while contained within the pen shell 1. The plurality of absorbent swab cartridges 2 is removably and serially positioned within the pen shell 1 between the refill end 12 and the dispensing end 11.

The cartridge advancement mechanism 3 is operatively integrated into the pen shell 1 and is configured to advance the plurality of absorbent cartridges toward the dispensing end 11 in such a way that a terminal cartridge from the plurality of absorbent cartridges may be manipulated by the user through the cartridge advancement mechanism 3 to protrude from the dispensing end 11 of the pen shell 1 for use, or to be completely ejected from the pen shell 1 and discarded after use. In some embodiments, the cartridge advancement mechanism 3 may further comprise means to lock in place along the pen shell 1. For example, the cartridge advancement mechanism 3 may be able to be selectively locked in one or more of a plurality of locking locations distributed between the refill end 12 and the dispensing end 11. In some embodiments, the cartridge advancement mechanism 3 grips one or more of the plurality of absorbent swab cartridges 2, and the user is able to advance or retract the plurality of absorbent swab cartridges 2 at their convenience.

Additionally or alternatively, in some embodiments, the cartridge advancement mechanism 3 may be integrated into the shell body or otherwise comprise such means as one or a plurality of stopper protrusions allowing the advancement mechanism and/or the plurality of cartridges to advance toward the dispensing end 11, but preventing movement back toward the refill end 12. In some embodiments, the pen shell 1 may further comprise one or more cartridge stopper protrusions connected within a lateral wall of the pen shell 1. Said stopper protrusions may be dimensioned and configured in conjunction with the plurality of absorbent swab cartridges 2 such that absorbent swab cartridges 2 are prevented from falling out of the dispensing end 11 during normal use but may be pressed completely out of the dispensing end 11 by the user through applying sufficient force to the advancement mechanism. It should further be noted that the components and form of the cartridge advancement mechanism 3 may vary in different embodiments, so long as the cartridge advancement mechanism 3 is able to move the plurality of absorbent swab cartridges 2 along the interior of the pen shell 1 toward the dispending end. In some embodiments, the cartridge advancement mechanism 3 may utilize a clicking action wherein the user presses a button found at the refilling end. Upon pressing the button, the cartridge advancement mechanism 3 will advance the plurality of absorbent swab cartridges 2 toward the dispensing end 11.

In the preferred embodiment, dispensed and discarded swab cartridges may be replaced by the user by inserting additional swab cartridges into the pen shell 1 through the refill end 12. Furthermore, the present invention preferably further comprises a cap that is removably attached to the pen shell 1 at the refill end 12 to prevent swab cartridges from falling out of the dispensing end 11 during normal use.

Figure 3:
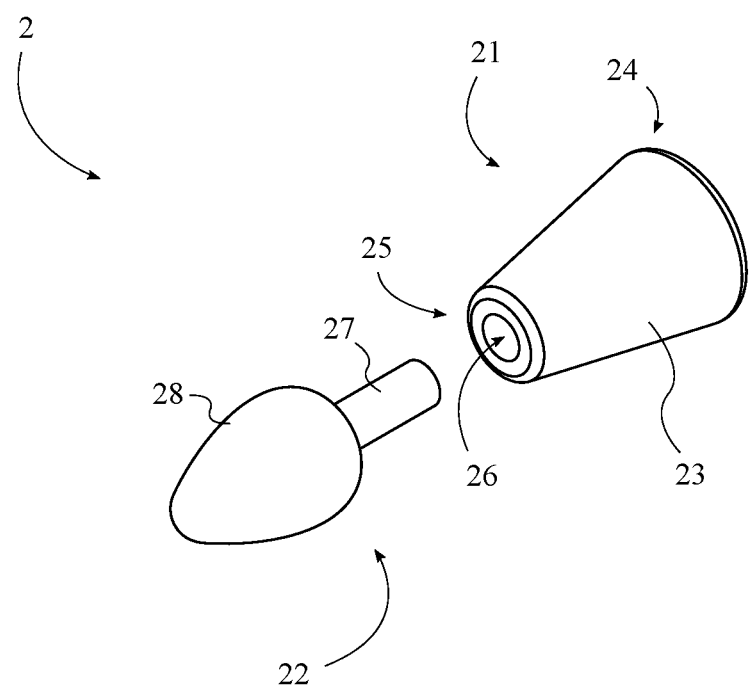
FIG. 3 is an exploded view of an absorbent swab cartridge.

It is contemplated that in various embodiments of the present invention, the plurality of absorbent swab cartridges 2 may vary in form according to various designs of the pen shell 1 and cartridge advancement mechanism 3. Referring to FIG. 3, in some embodiments of the present invention, each of the plurality of absorbent swab cartridges 2 comprises a holder 21 and an absorbent swab 22. Furthermore, the holder 21 comprises a holder body 23, a proximal end 24, a distal end 25, and a swab receiving cavity 26. The holder body 23 extends from the proximal end 24 to the distal end 25, and the swab receiving cavity 26 traverses into the distal end 25 of the holder body 23. The absorbent swab 22 is therefore positioned into the swab receiving cavity 26.

Furthermore, in some embodiments, the absorbent swab 22 comprises a stem 27 and an absorbent tip 28. The absorbent tip 28 is terminally connected adjacent to the stem 27, and the stem 27 is positioned into the swab receiving cavity 26. The stem 27 may be made of any material, such as, but not limited to, plastic, wood, or paper. In the preferred embodiment of the present invention, the absorbent tip 28 is made of cotton material, though other absorbent materials may be used in other embodiments, such as, but not limited to, rayon, silica, foam, or other material.

Figure 4:
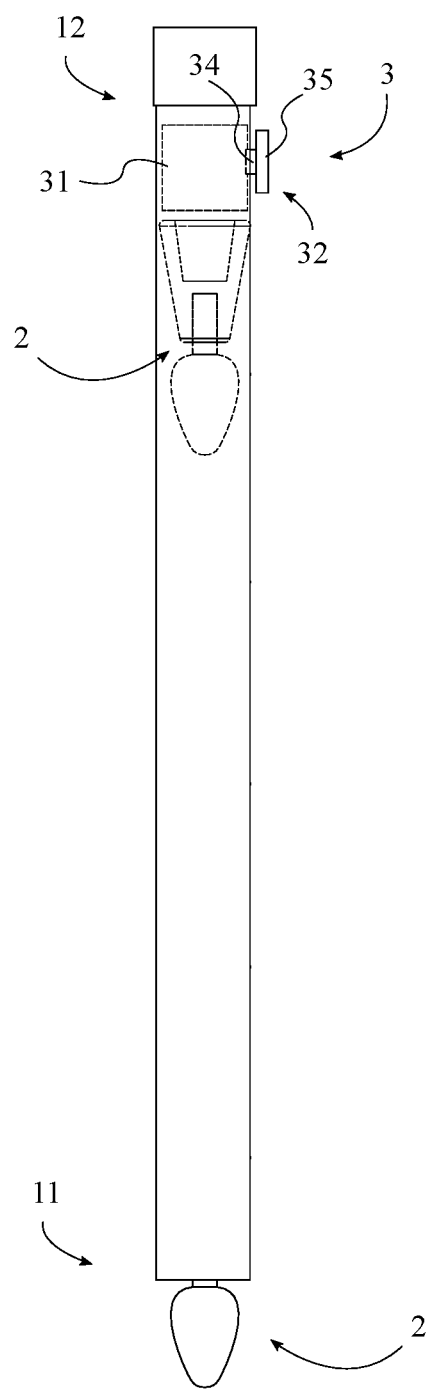
FIG. 4 is an internal side view of an embodiment of the present invention.

Referring to FIGS. 1 and 4, in some embodiments, the cartridge advancement mechanism 3 comprises a scroll insert 31, a scroll knob 32, and a slot 33. The slot 33 traverses through the pen shell 1 between the dispensing end 11 and the refill end 12. The scroll insert 31 is slidably positioned within the pen shell 1, the scroll knob 32 is connected to the scroll insert 31, and the scroll knob 32 traverses through the slot 33. The scroll insert 31 travels along the length of the pen shell 1, pressing against the plurality of absorbent swab cartridges 2 in order to advance the absorbent swab cartridges 2 toward the dispensing end 11. The scroll knob 32 is connected to the scroll insert 31 and is positioned exterior to the pen shell 1, providing the user with a feature with which to manipulate the scroll insert 31 within the pen shell 1.

Moreover, in some embodiments, the scroll knob 32 comprises a connecting portion 34 and a handling portion 35. The connecting portion 34 is perpendicularly connected to the scroll insert 31 and traverses through the slot 33. The handing portion is connected to the connecting portion 34 opposite the scroll insert 31, and thus is positioned exteriorly adjacent to the pen shell 1 opposite the scroll insert 31. Therefore, in the aforementioned configuration, the user is able to utilize the cartridge advancement mechanism 3 to manipulate the plurality of absorbent swab cartridges 2 toward the dispensing end 11 in order to discard a used cartridge or to move a new cartridge into position, protruding from the dispensing end 11, for use in removing or applying cosmetics.

In some embodiments, to use the present invention, the user first depresses a button located at the refilling end of the pen shell so it can hold a cotton swab in place to access the chamber. The user then reloads a stack of cotton swab cartridges into a tips hole. The tips hole may be at the dispensing end in this embodiment. The user then gently pushes the cotton swab stack fully into the pen shell until it clicks into place.

In the preferred embodiment, the benefits of the present invention are as follows. Each cotton swab stack or absorbent swab cartridge has a latex free casing. The present invention offers multiple use advantage with the plurality of swab cartridges, which may contain up to 20 or more dispensable absorbent swabs. The swab cartridges are refillable when depleted. The present invention is a travel size item that may be easily kept in any convenient location. The user does not have to worry about the possibility of spilling many loose individual swabs. The present invention is environment friendly and offers great economic value. The present invention is user friendly and reduces mess created by alternatives and may come in a variety of colors and may be used in beauty shops and salons.

Although the invention has been explained in relation to its preferred embodiment, it is to be understood that many other possible modifications and variations can be made without departing from the spirit and scope of the invention as hereinafter claimed.

What is claimed is:

1. A refillable absorbent swab applicator pen comprising:
a pen shell;
a plurality of absorbent swab cartridges;
a cartridge advancement mechanism;
the pen shell comprising a dispensing end and a refill end;
the pen shell extending between the dispensing end and the refill end;
the plurality of absorbent swab cartridges being removably and serially positioned within the pen shell between the refill end and the dispensing end;
the cartridge advancement mechanism being operatively integrated into the pen shell;
the cartridge advancement mechanism being configured to advance the plurality of absorbent swab cartridges toward the dispensing end;

each of the plurality of absorbent swab cartridges comprising a holder and an absorbent swab, the holder comprising a holder body, a proximal end, a distal end and a swab receiving cavity, the holder body extending from the proximal end to the distal end, the swab receiving cavity traversing into the distal end, the absorbent swab being positioned into the swab receiving cavity, the absorbent swab comprising a stem and an absorbent tip, the absorbent tip being terminally connected to the stem, the stem being positioned into the swab receiving cavity;

the cartridge advancement mechanism comprising a scroll insert, a scroll knob and a slot;

the slot traversing through the pen shell between the dispensing end and the refill end;

the scroll insert being slidably positioned within the pen shell;

the scroll knob being connected to the scroll insert;

the scroll knob traversing through the slot;

the scroll knob comprising a connecting portion and a handling portion;

the connecting portion being perpendicularly connected to the scroll insert;

the connecting portion traversing through the slot;

the handling portion being connected to the connecting portion opposite the scroll insert; and the handling portion being positioned adjacent to the pen shell opposite the scroll insert.

\* \* \* \* \*